(12) United States Patent
Muthuswamy et al.

(10) Patent No.: US 11,672,486 B2
(45) Date of Patent: Jun. 13, 2023

(54) DEVICE FOR NEUROPROSTHETICS WITH AUTONOMOUS TUNABLE ACTUATORS

(71) Applicants: Jitendran Muthuswamy, Chandler, AZ (US); Sivakumar Palaniswamy, Tempe, AZ (US)

(72) Inventors: Jitendran Muthuswamy, Chandler, AZ (US); Sivakumar Palaniswamy, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 296 days.

(21) Appl. No.: 17/035,068

(22) Filed: Sep. 28, 2020

(65) Prior Publication Data
US 2021/0121129 A1 Apr. 29, 2021

Related U.S. Application Data

(62) Division of application No. 15/136,126, filed on Apr. 22, 2016, now Pat. No. 10,835,184.
(Continued)

(51) Int. Cl.
*A61B 5/00* (2006.01)
*A61N 1/05* (2006.01)
(Continued)

(52) U.S. Cl.
CPC .......... *A61B 5/6877* (2013.01); *A61B 5/0004* (2013.01); *A61B 5/0031* (2013.01);
(Continued)

(58) Field of Classification Search
CPC ... A61B 5/6877; A61B 5/0004; A61B 5/0031; A61B 5/04001; A61B 5/0538;
(Continued)

(56) References Cited

U.S. PATENT DOCUMENTS 8,653,642 B2 2/2014 Sutanto
2007/0027371 A1 2/2007 Benaron
(Continued)

OTHER PUBLICATIONS

Jacskon et. al, "Long-term neural recordings using MEMS based movable microelectrodes in the brain". Frontiers in Nueroengineering, (Year: 2010).*
(Continued)

*Primary Examiner* — Adam Z Minchella
(74) *Attorney, Agent, or Firm* — Quarles & Brady LLP; Yakov Sidorin (57) ABSTRACT

A microelectromechanical device and method for neuroprosthetics comprises microactuators and microelectrodes. The microelectrodes are to be positioned in a nerve bundle and bonded with the microactuators through an interconnect. The position of each of the microactuators can be individually tuned through control signals so that the microelectrodes are implanted at desired positions in the nerve bundle. The control signals are transmitted to the microactuators and generated with a open-loop or closed-loop control scheme that uses signals acquired by the microelectrodes from the nerve bundle as feedback.

11 Claims, 9 Drawing Sheets

Related U.S. Application Data (60) Provisional application No. 62/151,316, filed on Apr. 22, 2015.

(51) Int. Cl.
*A61B 5/0538* (2021.01)
*A61B 5/24* (2021.01)
A61B 5/20 (2006.01)

(52) U.S. Cl.
CPC .............. *A61B 5/0538* (2013.01); *A61B 5/24* (2021.01); *A61B 5/6886* (2013.01); *A61N 1/0551* (2013.01); *A61B 5/202* (2013.01); *A61B 2562/028* (2013.01); *A61B 2562/0285* (2013.01); *A61B 2562/043* (2013.01)

(58) Field of Classification Search
CPC . A61B 5/6886; A61B 5/202; A61B 2562/028; A61B 2562/0285; A61B 2562/043; A61N 1/0551
See application file for complete search history.

(56) References Cited

U.S. PATENT DOCUMENTS

| | | | |
|---|---|---|---|
| 2008/0177196 A1 | 7/2008 | Burdick | |
| 2010/0268055 A1* | 10/2010 | Jung | A61B 5/6882 600/377 |
| 2012/0238936 A1 | 9/2012 | Hyde | |
| 2013/0134604 A1 | 5/2013 | Sutanto | |
| 2014/0329707 A1* | 11/2014 | Naughton | A61N 1/0536 600/300 |

OTHER PUBLICATIONS

Anand, Sindhu, "Towards adaptive micro-robotic neural interfaces: Autonomous navigation of microelectrodes in the brain for optimal neural recording", Dec. 2013, ProQuest LLC (Year: 2013).*
D. Ackermann et al., "Conduction Block of Peripheral Nerve Using High-Frequency Alternating Currents Delivered Through an Intrafascicular Electrode," Muscle & Nerve, 2010, vol. 41, pp. 117-119, 2010.
B. Dowden et al., "Muscle-Selective Block Using Intrafascicular High-Frequency Alternating Current," Muscle & Nerve, vol. 42, pp. 339-347, 2010.
M. Franke et al., "Combined KHFAC+DC Nerve Block Without Onset or Reduced Nerve Conductivity After Block," J. Neural Eng, vol. 11, 056012, 2014.
S. Chakrabarti et al., "Expert-Like Performance of an Autonomous Spike Tracking Algorithm in Isolating and Maintaining Single Units in the Macaque Cortex," J Neurosci Methods, vol. 205, pp. 72-85, 2012.
N. Jackson et al., "Long-Term Neural Recordings Using MEMS Based Movable Microelectrodes in the Brain," Frontiers in Neuroeng, vol. 3, pp. 1-13, 2010.
S. Kodandaramaiah et al., "Automated Whole-Cell Patch-Clamp Electrophysiology of Neurons In Vivo," Nature Methods, vol. 9, pp. 585-587, 2012.
M. Fee et al., "Miniature Motorized Microdrive and Commutator System for Chronic Neural Recording in Small Animals," J Neurosci Methods, vol. 112, pp. 83-94, 2001.
M. Wolf et al., "A Robotic Neural Interface for Autonomous Positioning of Extracellular Recording Electrodes," Int'l J Robotics Res, vol. 28, pp. 1240-1256, 2009.
J. Cham et al., "Semi-Chronic Motorized Microdrive and Control Algorithm for Autonomously Isolating and Maintaining Optimal Extracellular Action Potentials," J Neurophysiol, vol. 93, pp. 570-579, 2005.
A. Jackson et al., "Compact Movable Microwire Array for Long-Term Chronic Unit Recording in Cerebral Cortex of Primates," J Neurophysiol, vol. 98, pp. 3109-3118, 2007.

A. Gefen et al., "Are In Vivo and In Situ Brain Tissues Mechanically Similar?," J Biomech, vol. 37, pp. 1339-1352, 2004.
A. Sridharan et al., "Long-Term Changes in the Material Properties of Brain Tissue at the Implant-Tissue Interface," J Neural Eng, vol. 10, 066001, 2013.
A. Sharp et al., "In Vivo Penetration Mechanics and Mechanical Properties of Mouse Brain Tissue at Micrometer Scales," IEEE Trans Biomed Eng, vol. 56, pp. 45-53, 2009.
K. Miller et al., "Mechanical Properties of Brain Tissue In-Vivo: Experiment and Computer Simulation," J Biomech, vol. 33, pp. 1369-1376, 2000.
C. Chestek et al., "Long-Term Stability of Neural Prosthetic Control Signals From Silicon Cortical Arrays in Rhesus Macaque Motor Cortex," J Neural Eng, vol. 8, 045005, 2011.
M. Fee et al., "Variability of Extracellular Spike Waveforms of Cortical Neurons," J Neurophysiol, vol. 76, pp. 3823-3833, 1996.
G. Santhanam et al., "HermesB: A Continuous Neural Recording System for Freely Behaving Primates," IEEE Trans Biomed Eng, vol. 54, pp. 2037-2050, 2007.
J. Williams et al., "Long-Term Neural Recording Characteristics of Wire Microelectrode Arrays Implanted in Cerebral Cortex," Brain Res Protoc, vol. 4, pp. 303-313, 1999.
T. El Sayed et al., "Biomechanics of Traumatic Brain Injury," Comput Methods Appl Mech Eng, vol. 197, pp. 4692-4701, 2008.
L. Zhang et al., "A Proposed Injury Threshold for Mild Traumatic Brain Injury," ASME Trans J Biomech, vol. 126, pp. 226-236, 2004.
C. Bjornsson et al., Effects of Insertion Conditions on Tissue Strain and Vascular Damage During Neuroprosthetic Device Insertion, J Neural Eng, vol. 3, pp. 196-207, 2006.
W. Jensen et al., "In-Vivo Implant Mechanics of Flexible, Silicon-Based ACREO Microelectrode Arrays in Rat Cerebral Cortex," IEEE Trans Biomed Eng, vol. 53, pp. 934-940, 2006.
A. Sharp et al., "Toward a Self-Deploying Shape Memory Polymer Neuronal Electrode," J Neural Eng, vol. 3, pp. L23-L30, 2006.
G. McConnell et al., "Extraction Force and Cortical Tissue Reaction of Silicon Microelectrode Arrays Implanted in the Rat Brain," IEEE Trans Biomed Eng, vol. 54, pp. 1097-1107, 2007.
S. De et al., "Assessment of Tissue Damage Due to Mechanical Stresses," Int'l J Robotics Res, vol. 26, pp. 1159-1171, 2007.
S. Anand et al., "Electrothermal Microactuators With Peg Drive Improve Performance for Brain Implant Applications," J Microelectromech Syst, vol. 21, pp. 1172-1186, 2012.
J. Muthuswamy et al. "An Array of Microactuated Microelectrodes for Monitoring Single-Neuronal Activity in Rodents," IEEE Trans Biomed Eng, vol. 52, pp. 1470-1477, 2005.
J. Muthuswamy et al., "Electrostatic Microactuators for Precise Positioning of Neural Microelectrodes," IEEE Trans Biomed Eng, vol. 52, pp. 1748-1755, 2005.
C. Gold et al., "On the Origin of the Extracellular Action Potential Waveform: A Modeling Study," J Neurophysiol, vol. 95, pp. 3113-3128, 2006.
R. Britt et al., "Quantitative Analysis of Methods for Reducing Physiological Brain Pulsations," J Neurosci Methods, vol. 6, pp. 219-229, 1982.
M. Fee, "Active Stabilization of Electrodes for Intracellular Recording in Awake Behaving Animals," Neuron, vol. 27, pp. 461-468, 2000.
E. Branchaud, "A Control System for Positioning Recording Electrodes to Isolate Neurons in Extracellular Recordings," Calif Inst Tech, Thesis, 2006.
M. Green, "In Vivo Brain Viscoelastic Properties Measured by Magnetic Resonance Elastography," NMR in Biomed, vol. 21, pp. 755-764, 2008.
D. Van Gerwen et al., "Needle-Tissue Interaction Forces—A Survey of Experimental Data," Med Eng Phys, vol. 34, pp. 665-680, 2012.
J. Sutanto et al., "Packaging and Non-Hermetic Encapsulation Technology for Flip Chip on Implantable MEMS Devices," J Microelectromech Syst., vol. 21, No. 4, pp. 882-896, 2010.
Muthuswamy, NIH Project No. 1R21NS084492-01A1, "Autonomous MEMS Probes for Intracellular Recording", 2013, NIH. (Year: 2013).

\* cited by examiner

DEVICE FOR NEUROPROSTHETICS WITH AUTONOMOUS TUNABLE ACTUATORS

CROSS-REFERENCE TO RELATED APPLICATIONS

This application is a divisional of U.S. patent application Ser. No. 15/136,126, filed Apr. 22, 2016, which claims the benefit of U.S. Prov. Pat. App. Ser. No. 62/151,316, having the same title, filed Apr. 22, 2015, and incorporated fully herein by reference.

STATEMENT REGARDING FEDERALLY SPONSORED RESEARCH

This invention was made with government support under R01 NS055312 and R21 NS084492 awarded by the National Institutes of Health. The government has certain rights in the invention.

BACKGROUND

Devices for neural prosthetics are required to interact with neural tissue of the patient. Emerging prosthetic devices for the central and peripheral nervous system require interfaces that can stimulate or sense targeted neurons with high precision to achieve very specific functional states of the end-target organ. However, current neural interface and neuromodulation technologies lack the required stability and specificity to target specific sensory or motor neurons within a nerve bundle. These two attributes—stability and specificity—remain as the key challenges in developing chronic neural prosthetic technologies for central and peripheral nervous systems.

It would be desirable to have a device that can autonomously and precisely tune the position of the actuators of the neural prostheses to target a specific neuron in a nerve bundle.

SUMMARY

The present disclosure overcomes the aforementioned drawbacks by providing a microelectromechanical system (MEMS) device and method for neuroprosthetics comprising tunable microactuators and microelectrodes. The microelectrodes may be positioned in a nerve bundle and microbonded with the microactuators through an interconnect. The position of each of the microactuators can be individually tuned through control signals so that the microelectrodes are implanted at desired positions in the nerve bundle. The control signals are transmitted to the microactuators and generated with a closed-loop control scheme that uses signals acquired by the microelectrodes from the nerve bundle as feedback.

The device and method may further comprise a wireless telemetry where the wireless telemetry transmits recorded neurophysiologic signals acquired by the microelectrodes, microstimulation signals to the microelectrodes, and control signals of the microactuators. The wireless telemetry may communicate with the MEMS device through an interconnect or wirelessly. In one configuration, the interconnect is made of parylene polymer (poly para-xylylene) or polyimide, and connected via controlled collapse chip connection ("flip-chip") onto the MEMS device.

In one configuration, the MEMS device is used for blocking neural motor signals when the frequency of microstimulation signals is more than 1000 Hz.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present application discloses a microelectromechanical (MEMS) device where the position of microelectrodes can be precisely tuned and therefore end-organ functional states can be reliably achieved or detected. This is to solve the drawbacks of other implantable technologies in neuroprosthetics. One of such drawbacks is that implantable neuroprostheses cannot be tuned to target specific motor or sensory neurons in the nerve bundle and, as a result, cannot be used to reliably achieve or detect end-organ functional states, especially in chronic conditions.

The MEMS device disclosed in the present application can precisely interface with targeted motor or sensory neurons in a nerve fiber. The MEMS device has three major features: (i) MEMS microactuators cause sensors, such as microelectrodes or nanoelectrodes, to move individually and precisely within nerve bundles; (ii) microscale or nanoscale bonding technique that provides electrical and mechanical bonding between the microactuators and microelectrodes to be implanted in nerve fibers; and (iii) a closed-loop autonomous control scheme for precisely positioning microelectrodes within nerve fibers to stimulate and achieve optimal end-organ functions or detect end-organ functional states. The closed-loop control scheme works in combination with the microactuators and the microelectrodes.

Figures 1A, 1B, 1C:
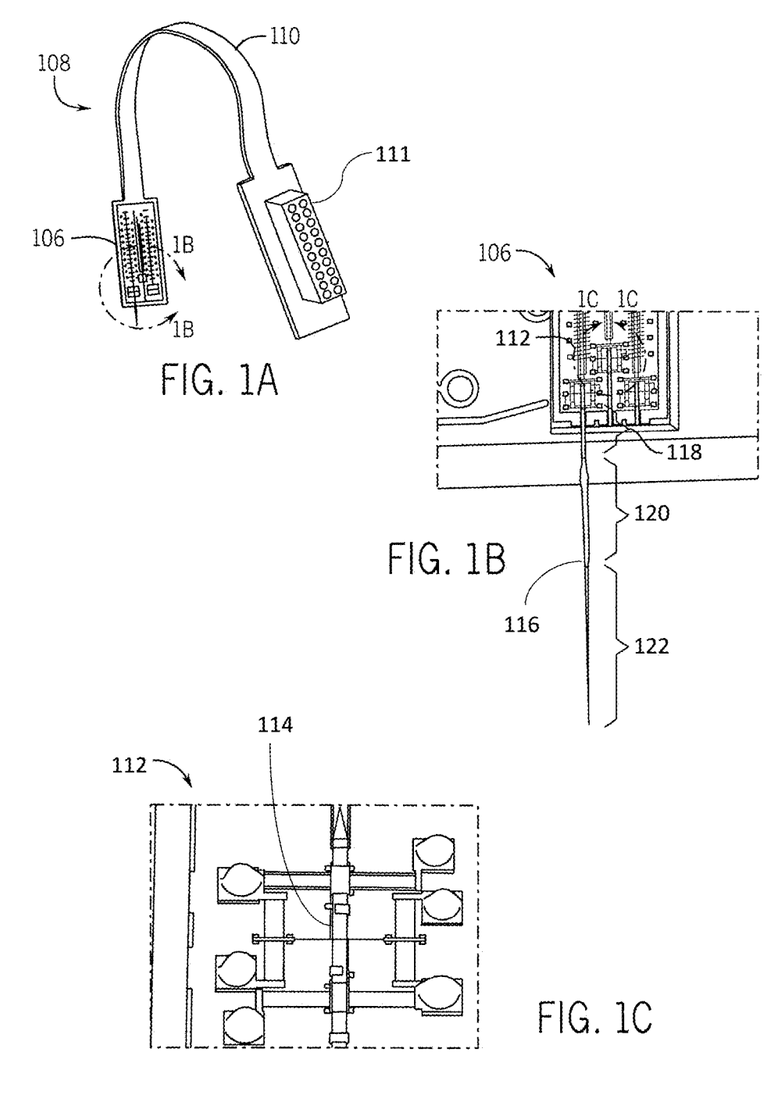
FIG. 1A is a top view of a MEMS device configured in accordance with the present application.
FIG. 1B is a top partial view of a MEMS chip of the MEMS device illustrated in FIG. 1A.
FIG. 1C is an enlarged partial view of the MEMS chip illustrated in FIG. 1B.
Figure 1D:
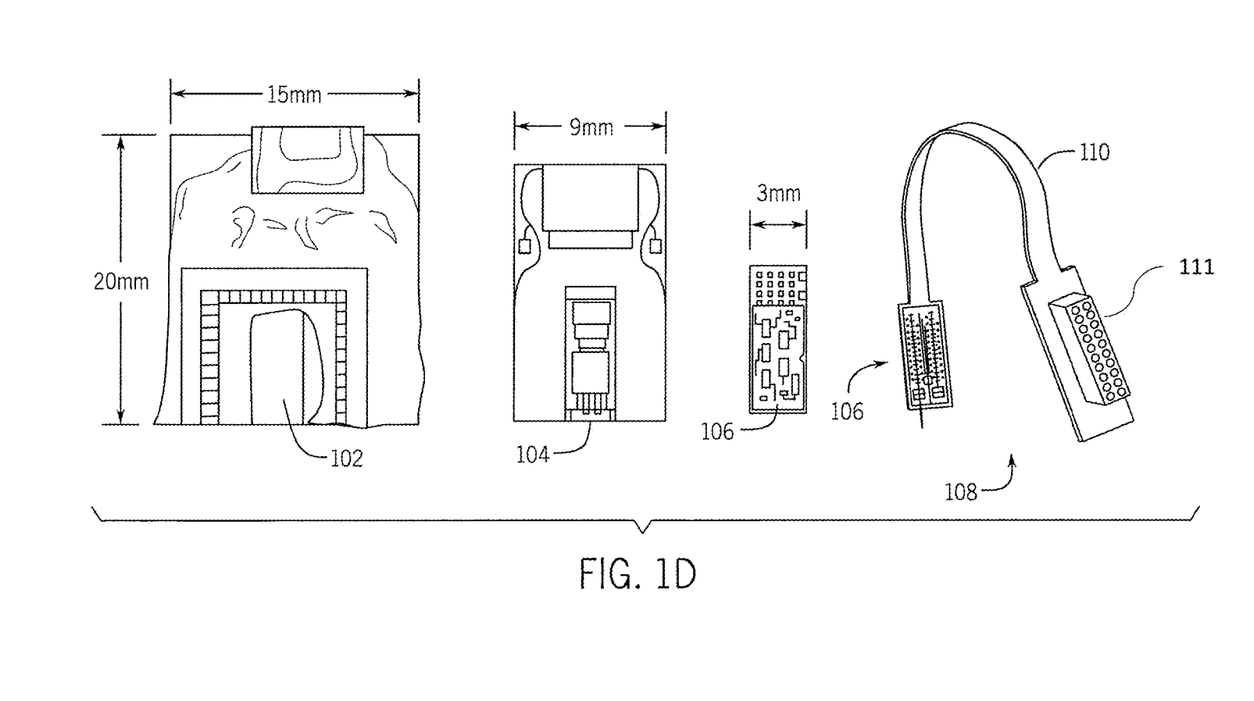
FIG. 1D is a top view of the MEMS device illustrated in FIG. 1A and other wire-bonding packages, with insets A-C showing increased resolution of components of the MEMS device.
Figure 8:
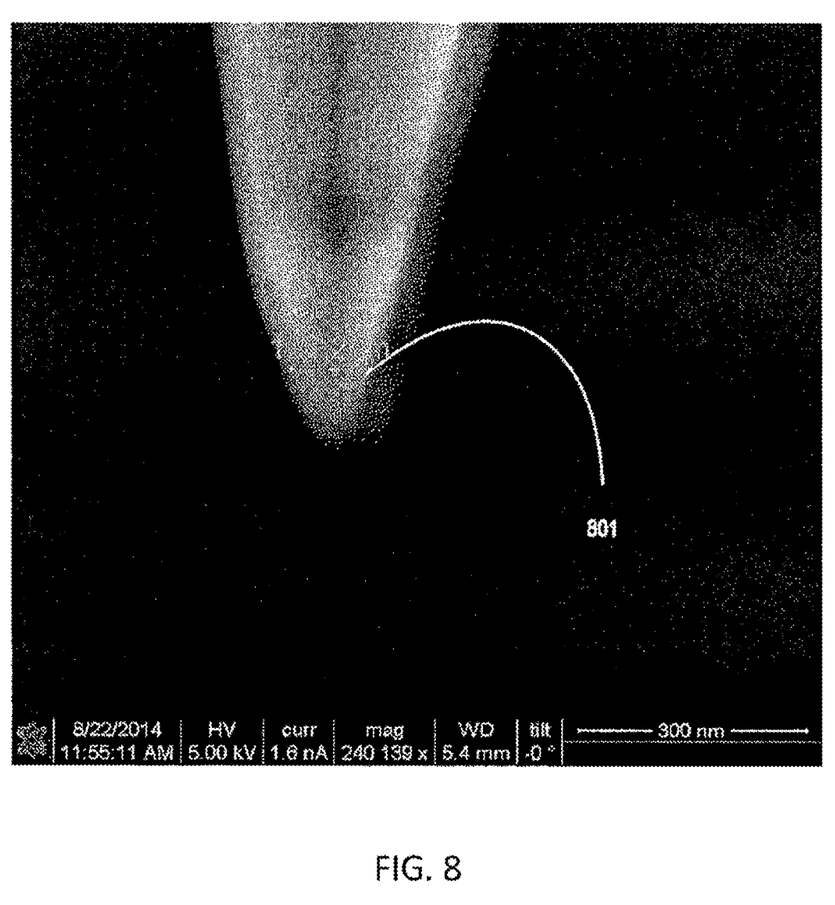
FIG. 8 illustrates a nanoelectrode.

Referring now to FIG. 1A, a MEMS device 108 configured in accordance with the present application may include a flip-chip packaged MEMS chip 106. In one configuration, chip-scale interconnects of the device are parylene or polyimide leads flip-chipped onto the MEMS chip 106 using a packaging approach as disclosed in U.S. Pat. No. 8,653,642. FIG. 1D provides a size comparison of the flip-chipped MEMS device to typical wire-bonding packaging. The flip-chip packaging drastically decreases the chip sizes from 15 mm in width for a wire-bonding packaged chip 102, to 9 mm for a MEMS die flip-chipped on a glass substrate, and again to 3 mm in width for flip-chip packaged chip 106. As shown in inset (A) (FIG. 1A), the MEMS chip 106 may be connected with a control unit 111 through a flexible parylene-C transmission ribbon 110. The control unit 111 transmits recorded neurophysiologic signals acquired by microelectrodes 116, microstimulation signals to be relayed to the microelectrodes 116, and control signals of microactuators 112 to or from the MEMS chip 106. In certain embodiments, a nanoelectrode 801 (FIG. 8) is used to acquire recorded neurophysiologic signals.

The MEMS device 108 may be implemented with an implantable MEMS microdrive technology, such as a chevron-peg drive as disclosed in *Electrothermal Microactuators with Peg Drive Improve Performance for Brain Implant Applications*, J MICROELECTROMECH SYST. 21(5):1172-1186, Jul. 13, 2012, by the present Applicants, incorporated fully herein by reference. Inset B (FIG. 1B) shows in an enlarged view a portion of the MEMS chip 106, depicting a microactuator 112 and a microbonded microelectrode 116 attached thereto. The microactuator 112 (shown in an enlarged view in inset C (FIG. 1C)) extends from an electrothermal strip 114 on the MEMS chip 106. The electrothermal strip 114 provides a voltage to the microactuator 112 to actuate it. The actuation moves the microelectrode 116, which is microbonded as described below.

The device 108 disclosed in the present application may use a microscale bonding technique for conductive mechanical interconnects. In one configuration, the microelectrode 116 includes a polysilicon microelectrode 118 attached to the microactuator 112 of the MEMS chip 106 and bonded to a conventional implant 122 (e.g., stainless steel or platinum-iridium microelectrode), with or without an insulation, via a polyimide interconnect 120. The interconnects 120 are filled with conductive material, such as silver epoxy. In certain embodiments, these interconnects 120 combine the capabilities of conventional implant 122, which are directly implanted in the nerves, for stimulation and recording with the tunable capabilities of the MEMS microactuators 112. In other embodiments, conventional implant 122 indirectly interface with the nerve tissue when it is inserted in a glass micropipette, which is filled with electrolytes that may include payloads such as drugs, DNA plasmids, siRNAs, miRNAs or other gene constructs.

In certain embodiments, the mechanical interconnect 120 also allows the microelectrodes 116 to enter into a nerve bundle perpendicularly even when the MEMS microactuators 112 are parallel to the nerve bundle. Further, in some embodiments, the mechanical interconnect 120 enables microelectrodes to enter into a nerve bundle at angles ranging from 0-180°. In turn, this allows a stable mounting of the MEMS device 108. Overall, the interconnects 120 improve the reach, directionality, and stimulation charge-injection ratios of the microactuators 112.

Figure 2A:
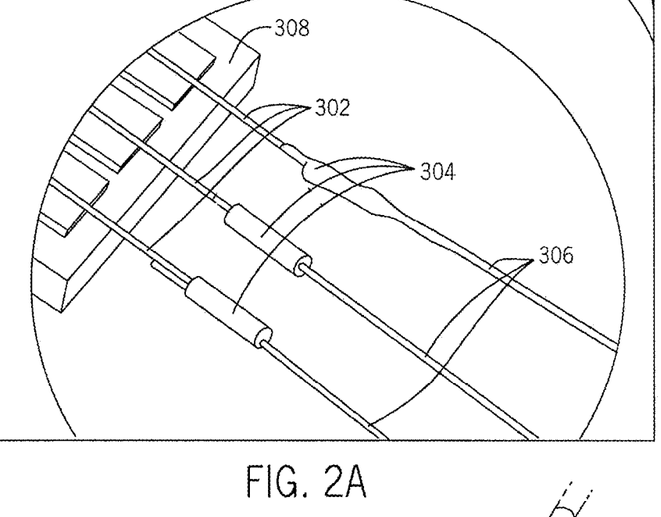
FIG. 2A is a top view of the microbonding between tunable microactuators and conventional microelectrodes of the MEMS device.
Figure 2B:
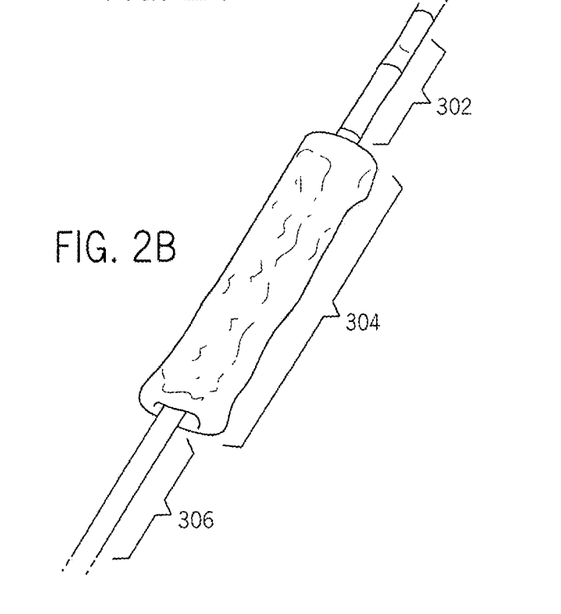
FIG. 2B is an enlarged view of an interconnect.

Referring now to FIG. 2A, another example MEMS chip 308 is provided to illustrate the microbonding. The chip 308 has three polysilicon thin film microelectrodes 302 each 50 µm wide. The conventional implant 306 has a diameter of 50 µm. The interconnects 304 in FIG. 2B are polyimide sleeves of 125 µm diameter filled with silver epoxy for conductive bond and microbond the polysilicon thin films from the MEMS chip 308 with the conventional implant 306.

Figure 3:
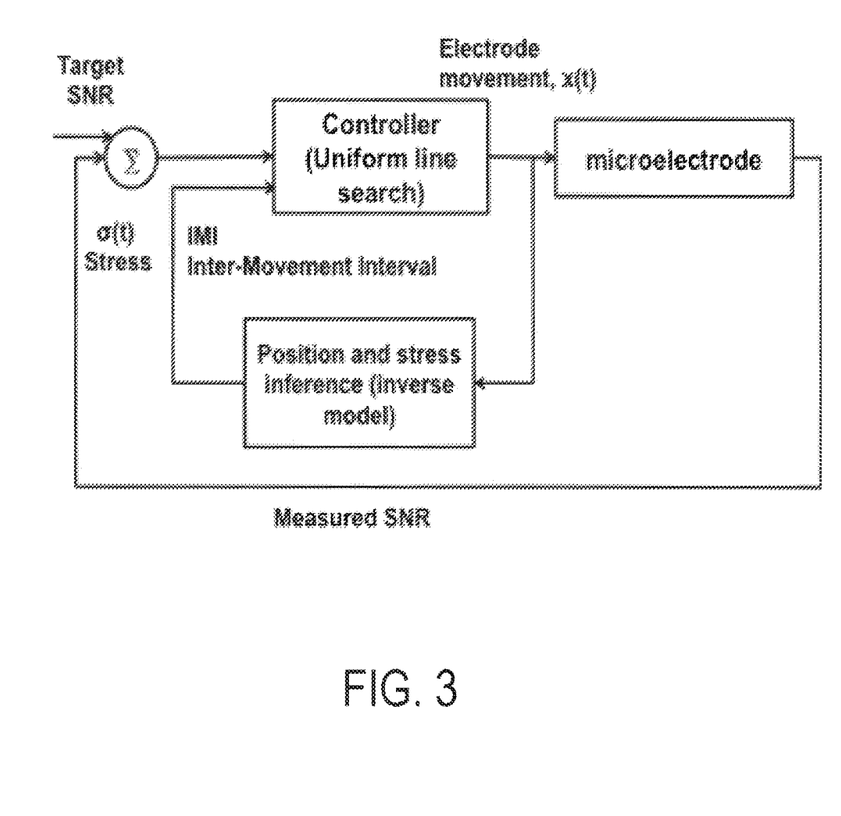
FIG. 3 is a diagram of a closed-loop control scheme of the MEMS device.

Referring to FIG. 3, the device disclosed in the present application uses a closed-loop control scheme to tune microelectrode positions. Based on quality of neural signal feedback—such as signal-to-noise ratio (SNR), and signal shapes and amplitudes, the microelectrodes in the MEMS device can be independently moved to optimize neural signal quality. See FIG. 4 for an example closed-loop control scheme for autonomously navigating the microelectrodes in a nerve to optimize SNR of recordings. In one configuration, the MEMS device is used for bladder control. During the stimulation phase, the bladder pressure is used as feedback to move any one of the microelectrodes to optimize the efficacy of stimulation. Other signals, such as an electrical impedance, current consumption, mechanical force, stress, and strain generated in surrounding tissue can also be used as feedback.

In one configuration, a TBSI (Triangle Biomedical Systems International, Durham, N.C.) combo headstage is used for wireless telemetry of neural data and neural stimulation signals. The TBSI has five channels (two redundant) for wireless recording and two channels for wireless stimulation. An application-specific integrated circuit (ASIC) can also be used for wireless telemetry. Besides wireless telemetry of neural, power, and stimulation, an ASIC can also be used for wireless telemetry of the signals controlling the MEMS microactuators. Wireless telemetry can be configured in various ways. For instance, data is wirelessly telemetered to an external computer that runs the control scheme. The external computer or a microcontroller returns with trigger signals wirelessly to the TBSI device, which in turn generates the control signals for movement of the microelectrodes. In another example, the entire control scheme can be on an ASIC.

The telemetry device for the MEMS device can communicate with the MEMS device through interconnects or wirelessly.

In one configuration, the number of channels—or microelectrodes—can be scaled up to 6-12 microelectrode systems by integrating an implantable ASIC with the MEMS chip. This increase of channels marginally increases form factors of the chips.

Figure 4:
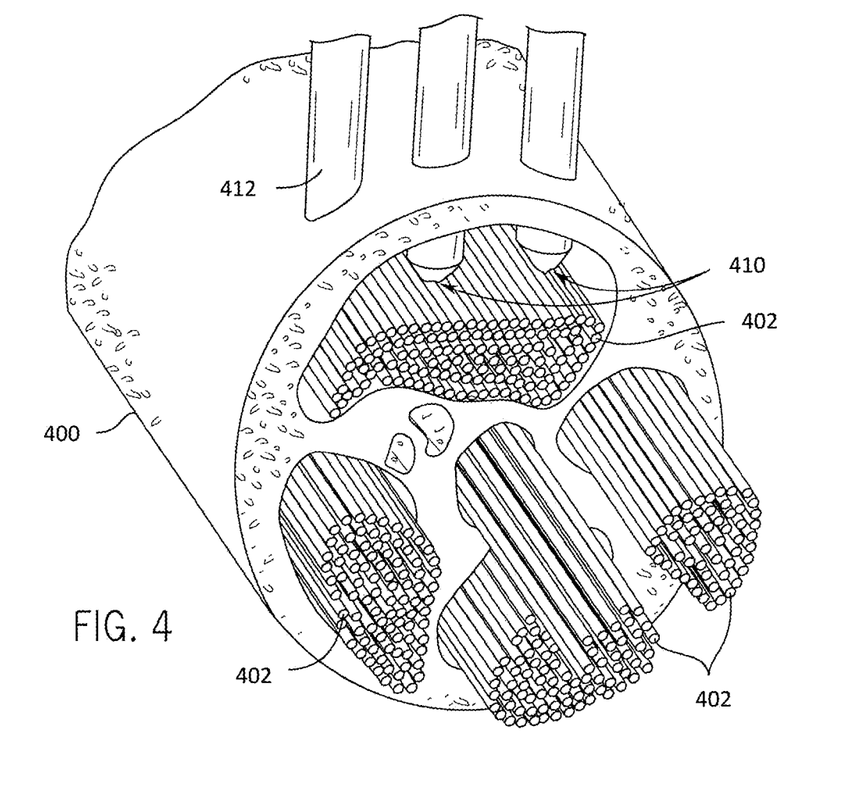
FIG. 4 is a cross-sectional perspective view of a nerve bundle showing microelectrodes of the MEMS device implanted into the nerve bundle.

FIG. 4 illustrates microelectrode implantation into a nerve 400. In one configuration, tunable MEMS microelectrodes 410 are slowly inserted into nerve bundles at locations that provide optimal motor control and sensing. In certain embodiments, the microelectrodes can move in steps of as small as about 6 microns. In other embodiments, the microelectrodes can move in steps of about 2 µm to 10 µm. As described herein, "about" means a 10% different in measurement. The timing between successive steps can be as large as the user desires to achieve stable interfaces without mechanical disruptions to other neural interfaces in the vicinity. To help the microelectrodes 410 of the MEMS device penetrate a nerve 400 and its nerve fascicles (or bundles) 402, the microelectrodes 410 may be covered in guide tubes 412 of certain shape or material for easy penetration into the nerve 400 and fascicles 402. Once the guide tubes 412 penetrate the nerve 400 and fascicles 402, the microelectrodes 410 emerge from the guide tubes 412 and are in contact with neurons. The spacing between the microelectrodes 410 can be as small as 125 µm. The position of each of the MEMS microactuators, and in turn the position of each of the microelectrodes 410, can be independently tuned in micrometer-scale (e.g., 6 µm) increments within the nerve bundle for optimal performance in chronic conditions. In one configuration, three microelectrodes 410 with peg-drive are used for recording or stimulating.

Individual microelectrodes 410 of the MEMS device can also move in steps if neural interactions or neural prosthetics need to change in time. The stepping process allows the microelectrodes 410 to interface with axons of peripheral nerves at very slow stepping rates (<10 µm/s). This low rate allows individual microelectrodes 410 to move between axons and other components of peripheral nerves with damage minimized. This process can be validated on a larger nerve like the sciatic nerve before used on a smaller nerve like the pelvic nerve.

Figure 5A:
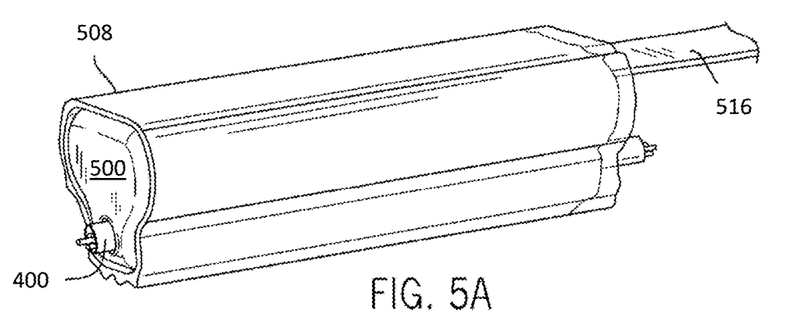
FIG. 5A is a left perspective view of a MEMS device interfacing with a nerve bundle.
Figure 5B:
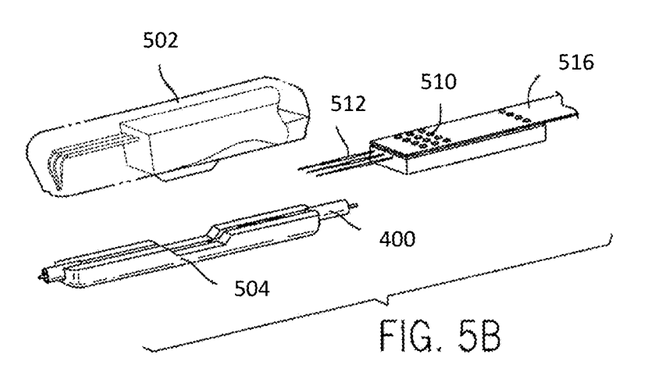
FIG. 5B is a cross-sectional view of the MEMS device of FIG. 5A showing microelectrodes interfacing with the nerve bundle and other components of the MEMS device.
Figure 5C:
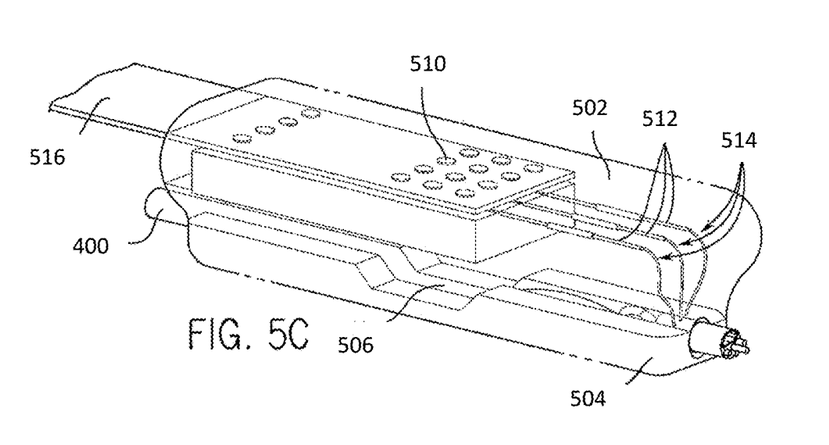
FIG. 5C is an exploded left perspective view of the MEMS device of FIG. 5A.

Referring now to FIGS. 5A-C, an example MEMS device is shown assembled around the nerve 400 of FIG. 4. An enclosure includes a top portion 502 and a bottom portion 504 that mate to enclose the nerve 400 within a channel 506 formed at the intersection of the portions 502, 504. The enclosure 500 may be made by 3D printing or another suitable manufacturing method. The enclosure 500 may be coated with a biocompatible silicone coat 508. A MEMS chip 510 may be held by the top portion 502 over the nerve 400. The microelectrodes 512 of the MEMS device extend from the MEMS chip 510 into guide tubes 514 that bend and guide the microelectrodes 512 into the nerve bundle as shown in FIG. 4. The guide tubes 514 allow the microelectrodes 512 parallel to the nerve 400 to penetrate the nerve 400. A polyimide or parylene transmission ribbon 516 can be flip-chipped onto the MEMS chip 510 and connects the MEMS chip 510 with a transceiver (i.e. control unit 111 of FIG. 1 or a telemetry device), such as a TBSI wireless headstage outside the animal. The MEMS device can also communicate wirelessly with a wireless telemetry device, such as an ASIC, without using the transmission ribbon 516.

Figure 6:
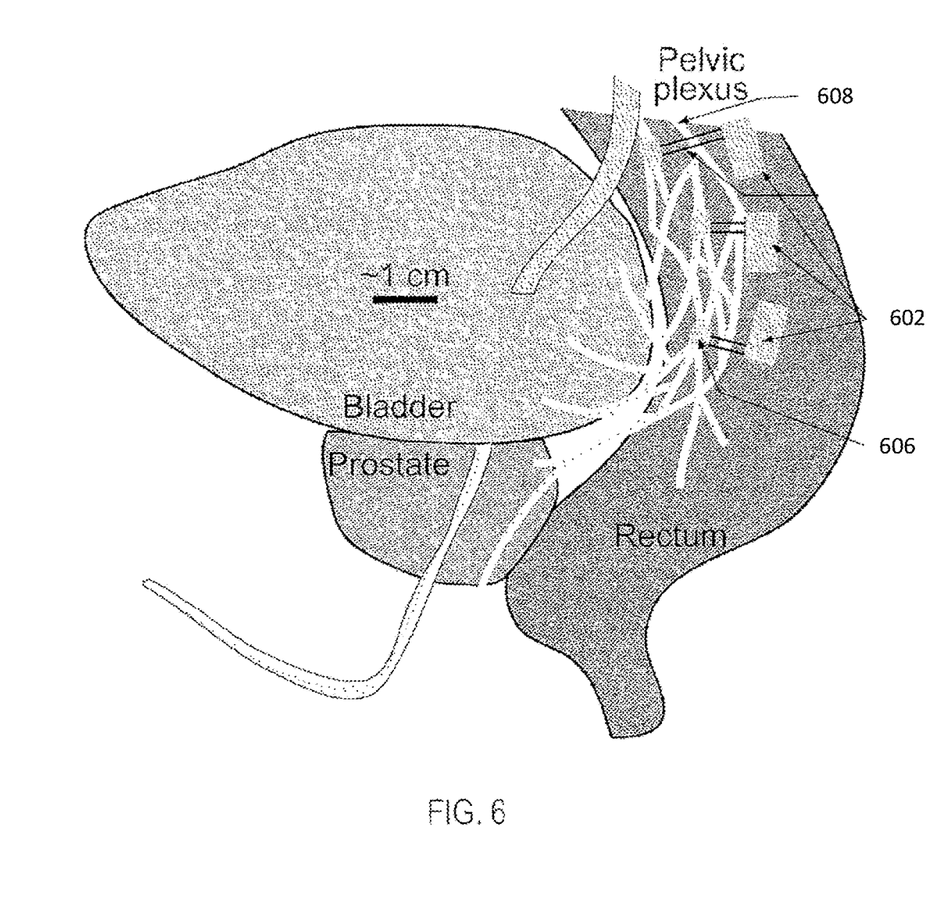
FIG. 6 is a schematic diagram of a plurality of MEMS devices implanted to control a bladder.

Referring now to FIG. 6, a schematic diagram depicting an example MEMS device implanted to control bladder is provided. Example MEMS devices 602 are implanted on pelvic plexus 608. The MEMS devices 602 are secured onto the pelvic plexus 608 by cuffs 606.

The MEMS device can be used for recording neurophysiologic signals from a nerve or micro-stimulating a nerve. The MEMS array microelectrodes are positioned within nerve bundles at locations that provide optimal motor control and sensing. Current passing-through electrodes are used for stimulation when the current frequency is ~20 Hz. When not stimulating or blocking, electrodes can detect local action potentials to monitor end-organ functional states.

Besides recording and stimulation, the MEMS microarrays can be used to block neural motor signals by using kilohertz frequency alternating current (KHFAC). Such current can be used to generate a local region of blocked axons, as demonstrated for intrafascicular electrodes in peripheral nerves. See PMID 19813186, D. Michael Ackermann, Jr. et al., *Conduction Block of Peripheral Nerve Using High Frequency Alternating Currents Delivered Through an Intrafascicular Electrode,* 41 MUSCLE & NERVE 117-19 (2010), available at http://www.ncbi.nlm.nih.gov/pmc/articles/PMC2947328/; PMID 20806397, Dowden B R et al., *Muscle-Selective Block Using Intrafascicular High-Frequency Alternating Current,* 42 MUSCLE & NERVE 339-47 (2010). Temporary DC stimulation can be used to alleviate potential onset responses to KHFAC. See PMID 25115572, Manfred Franke et al., *Combine KHFAC+DC Nerve Block Without Onset or Reduced Nerve Conductivity After Block,* 11 J. NEURAL ENGINEERING, Number 5, 2014.

Figure 7:
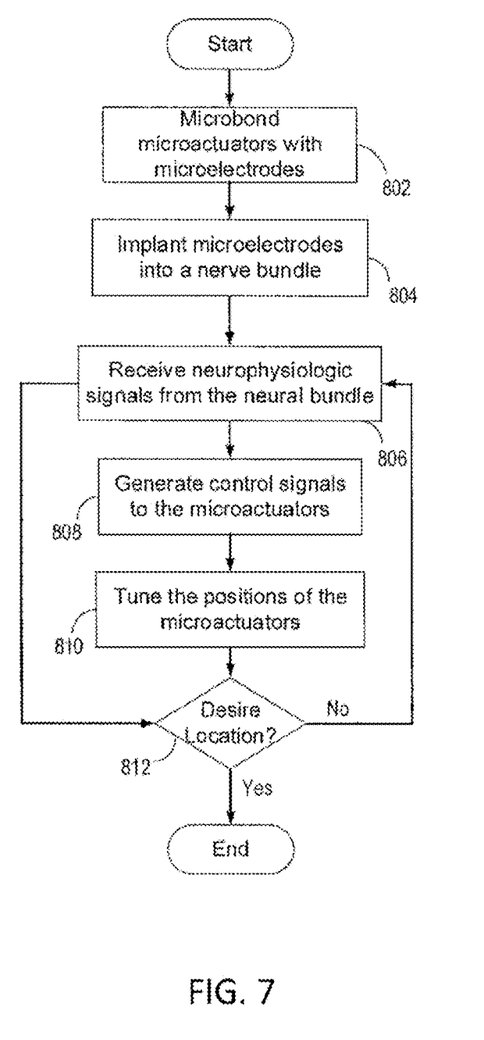
FIG. 7 is a flowchart of an example method implemented in accordance with the present application to precisely tune the positions of microelectrodes in a nerve bundle.

Referring now to FIG. 7, a flowchart depicting an example method used to precisely tune the positions of microelectrodes in a nerve bundle is provided. In step 802, polysilicon microelectrodes of a MEMS device are microbonded with conventional implants through interconnects. In step 804, the microelectrodes are implanted into a nerve bundle in micrometer-scale steps. In step 806, the MEMS device receives neurophysiologic signals from the neural bundle sampled by the implanted microelectrodes. In step 808, control signals of microactuators are generated and transmitted to the microactuators. In step 810, the positions of the microactuators are tuned under the control of the control signals. In step 812, the neurophysiologic signals sampled by the microelectrodes in step 806 are used as feedback in a closed-loop control scheme to determine whether the microelectrodes are at the desired positions in the nerve bundle. If the microelectrodes are not at the desired positions, the neurophysiologic signals are used to update control signals for the microactuators, which in turn control the tuning of the positions of the microelectrodes; once the microelectrodes are at the desired positions, the loop ends.

This MEMS tunable microelectrode array is scalable and can provide a multi-modal interface used for visceral organ-specific targets or peripheral somatic pathways. Specifically, it can be used for controlling urinary bladder, controlling bronchial tone or detecting airway resistance or conductance in the bronchial tree, sensing oxygen in the carotid body, controlling catecholamine secretion in the adrenal medulla, or controlling upper extremity robots as peripheral nerve prostheses.

The device disclosed in the present application can be used in the areas of biomarker, biosignature, central nervous system therapeutics, cyber-physical system, medical diagnostics, bioaugmentation, brain and machine interface, gene delivery, drug delivery, implantable medical device, MEMS, neural implants, neural prostheses, neurostimulation and neuromodulation, point of care, prosthesis, and medical sensors.

Examples

Experiments:

The following are experiments that can be used to test the device and method.

Experiment 1. Probe insertion tests in sciatic nerve can be done in acute experiments in 7 rodents. Rodent experiments lasting 7 days can be used to test the stability, signal quality, selectivity, and long-term performance of the integrated system in recording and stimulating axons in the sciatic nerve. The device can be powered with an external 500 mAh battery with an option for inductive powering.

Experiment 2. Target organ is bladder and the intervention point is preganglionic pelvic nerve. First start with five non-survival rat procedures. In these procedures, MEMS microarray placement and neuron identification can be established. Isoflurane anesthetized rats can be inserted with bladder and colon pressure catheters and their pelvic nerve can be exposed on one side. MEMS microarrays can be inserted in pelvic nerve fibers, followed by a bladder fill-void sequence. As needed, microarray probes depths can be adjusted in a step-wise fashion to optimize channel utility. At least three recording, stimulation, and blocking experiments should be performed, after successful stimulation parameters have been determined. Next, five survival experiments can be performed. MEMS microarray probes can be inserted in a way similar to that in the non-survival procedures. After a 7-day surgery recovery period, the animals can be lightly anesthetized and each of the recording, stimulation, and blocking experiments can be performed.

Other Technical Details in Key Areas:

The following are technical details in four key areas.

1. Probe insertion through epineurium. Peripheral nerves are different from cortical tissue. Inserting MEMS arrays into peripheral nerves while keeping the epineurium intact may be a challenge. The microelectrodes emerging from the guide tubes should be sharp to enable mechanical insertion through the epineurium using piezoelectric vibrations or linear force impulses. If needed, tapered ends for the guide tubes can be used in the package. The tapered ends can then guide the microelectrodes into the nerve bundle. Penetration through epineurium can be evaluated first in rat sciatic nerve experiments in Experiment 1 before pelvic nerve studies in Experiment 2. This way allows quick design modification and re-evaluation if needed.

2. Surgical attachment of the integrated package. The integrated package can be slightly larger in dimension than the pelvic nerve branches (see FIG. 6). The larger size has the potential to pull on the nerve. A fitted silicone cuff can be used to maintain stability of the package on the nerve and eliminate any relative motion between the package and the nerve. The cuff can first be evaluated with larger sciatic nerves in Experiment 1 before using it in smaller pelvic nerves in Experiment 2.

3. Identifying bladder axons of interest. The design of the MEMS arrays disclosed in the present application allows for individual probes to be positioned at optimal locations. Brief duration of a rat surgery may limit success rates in positioning probes at optimal locations within the rat pelvic nerve. This can be mitigated by using multiple probes for each function (recording, stimulation, or blocking) and first insert probes partially into the nerves (18-60 µm) before beginning bladder fill trials for neuron identification. After one or more bladder fill and neuron identification sequence, electrode probe positions can be adjusted in increments of 6 µm to optimize the afferent/efferent channel counts. The control approach used during the positioning is similar to that shown in FIG. 3.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for positioning a sensor of a microelectromechanical device (MEMS device) within a nerve bundle of a subject, the method comprising:
   providing one or more sensors, each sensor comprising an electrode portion made of polysilicon, an implant portion made from stainless steel, and an interconnect portion extending the electrode portion into the implant portion and electrically and structurally bonding the electrode and implant portions with one another;
   implanting the one or more sensors into the nerve bundle;
   receiving from the nerve bundle, at the one or more sensors, signals characterizing the nerve bundle, said signals including neurophysiologic signals and electrical impedance signals; and
   responsive to received signals, moving a distal end of the implant portion first electrode upwardly or downwardly within the nerve bundle to optimize the received signals.

2. The method of claim 1, wherein moving the distal end of the implant portion comprises:
   generating one or more control signals using a closed-loop control scheme, of said MEMS device, that uses the neurophysiological signals; and
   sending the one or more control signals to one or more microactuators in signal communication with the one or more sensors to adjust a position of the implant portion by the one or more microactuators so that the corresponding implant portions of the one or more sensors are implanted at optimal positions in the nerve bundle.

3. The method of claim 2, wherein the moving the distal end of the implant portion further comprises utilizing other signals selected from the group consisting of, a current consumption signal, a stress signal, and a strain signal each generated in surrounding tissue of the nerve bundle as feedback.

4. The method of claim 1, wherein the providing includes providing said implant portion configured as a microelectrode.

5. The method of claim 1, wherein the providing includes providing said implant portion configured as a nanoelectrode.

6. The method of claim 1, wherein said implanting includes implanting the implant portion of the one or more sensors along an axis that is transverse to the corresponding electrode portion of the one or more sensors.

7. The method of claim 1, wherein said implanting includes implanting the implant portion of the one or more sensors transversely to the nerve bundle while a microactuator of the MEMS device is parallel to the nerve bundle.

8. The method of claim 1, wherein the implant portion of the one or more sensors is covered with a guide tube, and wherein said implanting includes penetrating the nerve bundle with the guide tube and emerging the implant portion from inside the guide tube to establish contact between the implant portion and a neuron.

9. The method of claim 1, further comprising enclosing the nerve bundle within a channel of the MEMS device wherein the implanting includes implanting a bent sensor.

10. The method of claim 1, wherein the implanting includes implanting the implant portion of a spatially bent sensor through a guide tube covering said implant portion.

11. The method of claim 1, further comprising blocking neural motor signals of said nerve bundle with the use of alternating current.

* * * * *